(12) United States Patent
Een et al.

(10) Patent No.: US 8,449,519 B2
(45) Date of Patent: May 28, 2013

(54) SEAM JOINING TOGETHER AT LEAST TWO WEB MATERIALS

(75) Inventors: Hans Een, Mölnlycke (SE); Marcus Lehto, Fotö (SE); Ulrika Carlson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 483 days.

(21) Appl. No.: 12/741,352

(22) PCT Filed: Dec. 20, 2007

(86) PCT No.: PCT/SE2007/001144
§ 371 (c)(1),
(2), (4) Date: May 4, 2010

(87) PCT Pub. No.: WO2009/082277
PCT Pub. Date: Jul. 2, 2009

(65) Prior Publication Data
US 2010/0268183 A1    Oct. 21, 2010

(51) Int. Cl.
*A61F 13/15*         (2006.01)

(52) U.S. Cl.
USPC ................. 604/396; 604/385.31; 604/392

(58) Field of Classification Search
USPC .................................. 604/396, 385.31, 392
See application file for complete search history.

(56) References Cited

U.S. PATENT DOCUMENTS

| | | |
|---|---|---|
| 4,205,679 A | 6/1980 | Repke et al. |
| 4,938,817 A | 7/1990 | Langley |
| 5,163,932 A | 11/1992 | Nomura et al. |
| 5,226,992 A | 7/1993 | Morman |
| 5,626,574 A | 5/1997 | Sasaki et al. |
| 5,919,539 A | 7/1999 | Bisbis et al. |

(Continued)

FOREIGN PATENT DOCUMENTS

| | | |
|---|---|---|
| EP | 0 646 062 B1 | 8/1996 |
| EP | 1 035 818 A1 | 9/2000 |

(Continued)

OTHER PUBLICATIONS

An English Translation of the Office Action (Notice of Reasons for Rejection) dated Jul. 3, 2012, issued in corresponding Japanese Patent Application No. 2010-539347. (3 pages).

(Continued)

*Primary Examiner* — Jacqueline F. Stephens
(74) *Attorney, Agent, or Firm* — Buchanan Ingersoll & Rooney PC

(57) ABSTRACT

A seam joining together at least two web materials in an overlapped manner by ultrasonic welding, heat bonding or the like, in a bonding pattern, which includes comprising a first bonding pattern and at least one second bonding pattern extending in a longitudinal direction along and adjacent at least one side edge of the overlapped portion. The bonded area of the second bonding pattern occupies more than 30% of the combined bonded area of the first and second bonding patterns. The bonding elements of the first bonding pattern have a mean area that is at least 2 times the mean area of the bonding elements of the second bonding pattern. The contact area of the bonding pattern, as seen in transverse direction of the seam, is between 10 and 30% of the width of the bonding pattern at any given point along the length of the bonding pattern.

22 Claims, 5 Drawing Sheets

U.S. PATENT DOCUMENTS

| | | |
|---|---|---|
| 6,713,159 B1 | 3/2004 | Blenke et al. |
| 2004/0116889 A1 | 6/2004 | Carbone, II et al. |
| 2006/0089616 A1 | 4/2006 | Belau et al. |
| 2009/0292266 A1* | 11/2009 | Back ............................ 604/365 |

FOREIGN PATENT DOCUMENTS

| | | |
|---|---|---|
| GB | 1 332 037 A | 10/1973 |
| JP | 3069885 U | 7/2000 |
| JP | 2000-279444 A | 10/2000 |
| JP | 2006-006780 A | 1/2006 |
| WO | WO 98/29251 A1 | 7/1998 |
| WO | WO 99/27876 A1 | 6/1999 |
| WO | WO 01/00129 A1 | 1/2001 |
| WO | 02/18125 A2 | 3/2002 |
| WO | WO 03/000165 A1 | 1/2003 |
| WO | WO 03/047488 A1 | 6/2003 |
| WO | WO 2004/017885 A1 | 3/2004 |
| WO | 2007/067103 A1 | 6/2007 |
| WO | WO 2008/008004 A1 | 1/2008 |

OTHER PUBLICATIONS

International Search Report dated Sep. 19, 2008.
Written Opinion of the International Searching Authority dated Sep. 19, 2008.

* cited by examiner

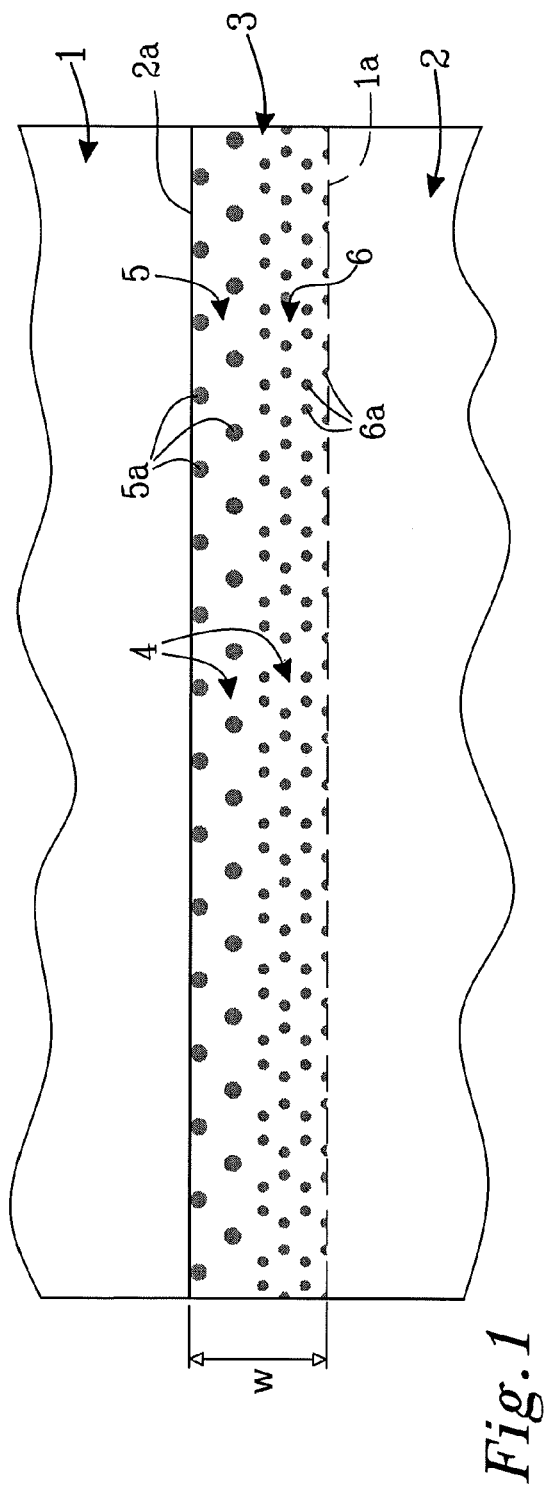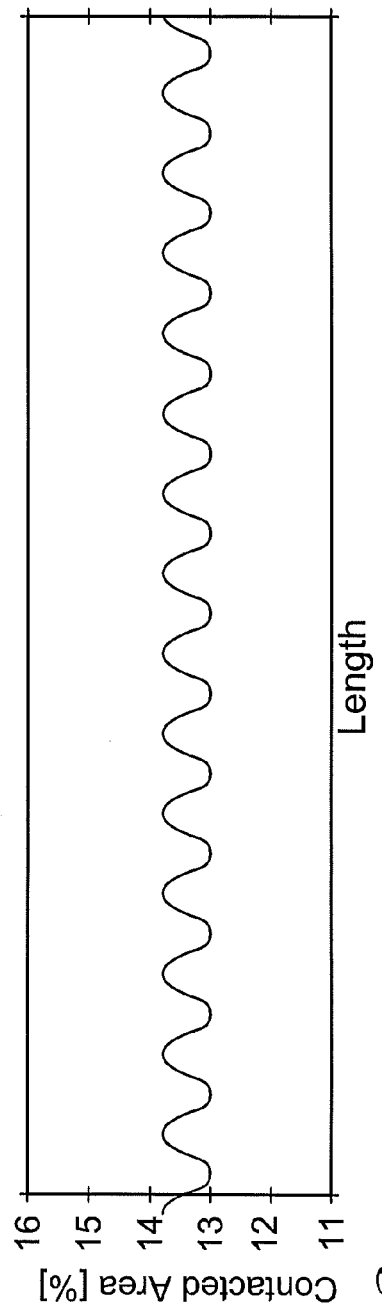

SEAM JOINING TOGETHER AT LEAST TWO WEB MATERIALS

TECHNICAL FIELD

The present invention refers to a seam joining together at least first and second web materials, at least one of which comprises heat fusible material, the first web material having a side edge overlapping with a side edge of the second web material, wherein an overlapped portion is formed where said web materials overlap. The web materials in said overlapped portion are bonded together in a bonding pattern extending over at least a part of the overlapped portion to form said seam. The bonding pattern is accomplished by forwarding the web materials through a bonding apparatus, such as an ultrasonic welding apparatus, heat bonding apparatus or the like.

BACKGROUND OF THE INVENTION

Web materials comprising heat fusible material, either fibrous webs, films or laminates thereof, are used in a variety of applications, such as protective clothing and hygiene articles, especially disposable absorbent personal care articles, like diapers, sanitary napkins and incontinence guards. In most of such applications the web materials must be joined, which is conventionally done by ultrasonic welding, heat bonding, laser welding or by adhesive. Bonding by ultrasonic welding, heat bonding or laser welding is usually done by forming a bonding pattern comprising a plurality of bonding elements in which the heat fusible components of the web materials are fused and thus bonded together.

The bonding is done in a process line, in which material variations as well as process variations may occur, which can effect the exact positioning of the bonding pattern with respect to the overlapping side edges of the web materials. If the bonding pattern ends up being located a bit offset with respect to the overlap, an edge of the overlap may protrude from the surface of the joined web materials. This will reduce the quality of the seam and of the article and if used in an article worn against the skin of a wearer such a protruding edge may cause skin irritations.

U.S. Pat. No. 5,919,539 discloses ultrasonic seaming of spunbonded polyolefin sheets for example used in protective clothing. The overlapping sheet edges are fed between an ultrasonic horn and a patterned roll that has a raised pattern corresponding to the desired bonding pattern. A waffle-like bonding pattern is created and the edges of the sheet are welded over so as to eliminate protruding sheet edges along the seam.

U.S. Pat. No. 5,626,574 refers to a disposable diaper having a front and a back body panel bonded to each other by ultrasonic welding to form side seams. The welded side seams are defined by patterns of intermittently arranged bonding elements of different shape. The purpose is to create a welding pattern which allows the side seams to be torn open longitudinally along the welded zones.

U.S. Pat. No. 4,938,817 shows a welding pattern for joining two overlapping material webs, said welding pattern comprises short dashed lines extending in parallel to the edges of the fabric.

U.S. Pat. No. 4,205,679 discloses a disposable undergarment in which a strong ultrasonic weld seam is formed by a plurality of weld lines extending in longitudinal direction of the overlapping side edges spaced inwardly from the edges of the overlap.

U.S. Pat. No. 6,713,159 discloses a tear-resistant bond pattern in a seam in an absorbent article, said bond pattern comprising a first sub-array of separate longitudinally oriented bond elements proximate each side edge of the seam and a second sub-array of separate longitudinally oriented bond elements disposed inwardly of the side edges. The first sub-array of bond elements acts as stress receptor elements and the first sub-array of bond elements acts as transfer and dissipation elements.

WO 2004/017885 discloses a bonding pattern in a seam in an absorbent article, said bonding pattern comprising a plurality of bond points oriented in such a way as to allow the bond pattern area to stretch from 8 to 30%.

GB patent no. 1 332 037 discloses a weld seam between two thermoplastic fabrics wherein the bonding pattern comprises a plurality of bonding elements located along two lines at the edges of the seam and further bonding elements located between these two lines.

The international patent application PCT/SE2006/00858 refers to a seam having a bonding pattern comprising a main bonding pattern and at least one edge bonding pattern extending along at least a part of at least one side edge of the overlapped portion, wherein the bonded area of said edge bonding pattern occupies not more than 30% of the total bonded area of the central bonding pattern plus the bonded area of the edge bonding pattern.

There is a however still a need for improved bonding patterns for seams joining together at least two web materials of the above mentioned kind, said bonding pattern providing both a strong seam along the overlap and a reduced risk for protruding edges along the seam.

OBJECT AND MOST IMPORTANT FEATURES OF THE INVENTION

The present invention aims at solving the problem set out above and to provide a bonding pattern with optimized strength properties and finish along the seam edge. These and further objects have been provided by a bonding pattern comprising a plurality of bonding elements spaced from each other in a repeating pattern, said overlapped portion having a pair of longitudinal side edges defined by said overlapping side edges of the web materials, said bonding pattern having a length and a width defined by first and second side edges of the bonding pattern. The bonding pattern comprises a first bonding pattern extending in longitudinal direction along at least a part of the overlapped portion, and at least one second bonding pattern extending in longitudinal direction along and adjacent at least a part of at least one of said side edges of said overlapped portion. The bonded area of said second bonding pattern occupies more than 30% of the combined bonded area of the first bonding pattern and the bonded area of the second bonding pattern. The bonding elements of the first bonding pattern have a mean area that is at least 2 times larger than the mean area of the bonding elements of the second bonding pattern, and the contact area of the bonding pattern, as seen in the transverse direction, is between 10 and 30% of the width of the bonding pattern at any given point along the length of the bonding pattern.

The combined first and second bonding patterns provide for a seam with high strength and a reduced tendency to tear along the edges as well as having a neat finish along the seam edge with a reduced risk for edges protruding along the seam.

In one embodiment the bonded area of the second bonding pattern occupies at least 50%, preferably at least 60% of the total bonded area occupied by the combined first and second bonding pattern.

In one aspect of the invention the bonded are of the second bonding pattern is not more than 75% of the total bonded area occupied by the combined first and second bonding pattern.

The bonding elements of the first bonding pattern may in one embodiment have a mean area that is at least 2.5 times, preferably at least 3 times and more preferably at least 4 times larger than the mean area of the bonding elements of the second bonding pattern.

The bonding elements of the second bonding pattern may in a further embodiment each have an area of not more than 4 mm$^2$, preferably not more than 3 mm$^2$ and more preferably not more than 2 mm$^2$.

In one aspect of the invention the contact area, as seen in the transverse direction, x, of the combined first and second bonding pattern is between 10 and 25% and preferably between 13 and 20% of the width, w, of the bonding pattern at any given point along the length of the bonding pattern.

The second bonding pattern may in one embodiment comprise a plurality of small bonding elements each having a mean area of not more than 2 mm$^2$, said bonding elements being arranged in at least two longitudinal rows in which the bonding elements are located in a staggered relationship with respect to the bonding elements of the adjacent row, and wherein the number of bonding elements in the second bonding pattern is between 8 and 50 per cm$^2$.

The first bonding pattern may also comprise a plurality of bonding elements arranged in at least two longitudinal rows in which the bonding elements are located in a staggered relationship to each other. The bonding elements of the first bonding pattern may further be located offset with respect to the bonding elements of the second bonding pattern as seen in the transverse direction.

In a further embodiment the number of bonding elements in the first bonding pattern is between 4 and 25 per cm$^2$.

In one aspect of the invention the bonding elements of the second bonding pattern are circular. In a further aspect the bonding elements of the first bonding pattern are circular According to one embodiment said bonding pattern comprises two edge bonding patterns, one on each side of the central bonding pattern.

The width of the overlapped portion in transverse direction, x, is according to one embodiment between 5 and 40 mm preferably between 6 and 20 mm. The width, w, of the bonding pattern, i.e. the combined first and second bonding pattern is according to a further embodiment between 5 and 40 mm, preferably between 6 and 20 mm.

The first bonding pattern has according to one embodiment a bonding density of at least 2% and not more than 60%, preferably not more than 40%. The second bonding pattern has according to a further embodiment a bonding density of between 5 and 60%, preferably between 10 and 50%. In one aspect of the invention the second bonding pattern has a higher bonding density than the first bonding pattern.

In one aspect of the invention the web materials have a combined basis weight between 25 and 130 g/m$^2$ in said overlapped portion.

In a further aspect of the invention at least one of the web materials is an elastic material.

In one embodiment the seam is located in the same plane as the web materials that are joined together.

In a still further aspect the seam is present in a personal care absorbent article comprising an absorbent structure and first and second web materials comprising heat fusible material joined together to form said seam.

The personal care absorbent article is in one embodiment a pant-like garment comprising a first body panel, a second body panel and a crotch portion there between, said first and second body panels being joined together in an overlapped manner by a bonding pattern as described to form side connections forming said seam.

In a further embodiment the personal care absorbent article is a pant-like garment comprising a first body panel, a second body panel and a crotch portion there between, said first and second body panels being joined together to form side connections and further being provided with an elastic waistband, said waistband being joined to the first and/or second body panels in an overlapped manner by a bonding pattern as described, to form said seam.

In a still further embodiment the personal care absorbent article is an absorbent garment such as a diaper and an incontinence guard comprising a first body panel, a second body panel and a crotch portion there between, each of said first and second body panels having a waist portion, said garment further being provided with opposed laterally extending belt members attached to the waist portion of the first body panel and being adapted to be wrapped around the waist of the wearer of the garment and fastened together by means of first fastening means, the second body panel at its waist portion being provided with second fastening means adapted to be fastened to the belt members, in such a way that the garment will assume a pant-like shape, said belt members being joined to first body panel in an overlapped manner by a bonding pattern as described to form said seam.

BRIEF DESCRIPTION OF THE DRAWINGS

The invention will in the following be closer described with reference to some embodiments shown in the accompanying drawings.

FIG. 1 shows a welded seam between two overlapping web materials having a bonding pattern according to the invention.

FIG. 2 is a graph showing the lengthwise surface coverage of the bonding pattern of FIG. 1.

DEFINITIONS

Figure 3:
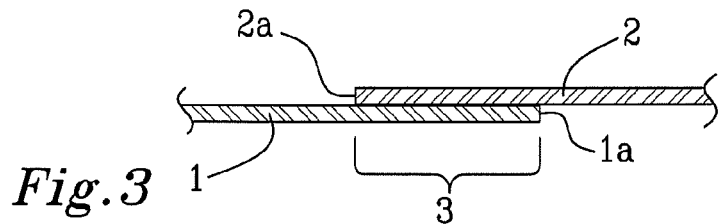
FIG. 3 is a side view of a seam between two web materials in which the seam is located in the same plane as the web materials.

"Bonding element area" is the geometric area occupied by a bonding element. In the case of bonding elements of different areas the mean bonding element area can be calculated. For hollow bonding elements, for example in the form of a ring, the bonding element area is defined by the area enclosed by the outer circumference of the bonding element (including the hole).

"Bonded area" is the area of a bonding pattern that is occupied by bonding elements.

"Bonding density" is defined as the area occupied by bonding elements in relation to the entire area circumscribed by the bonding pattern including the non-bonded areas between bonding elements.

"Contact area" in transverse direction of a the bonding pattern is a weighted mean value of the area of contact between the bonding apparatus (for example ultrasonic horn and pattern roll) and the web materials as seen in transverse direction of the seam and is determined according to the description below.

DESCRIPTION OF PREFERRED EMBODIMENTS

FIG. 1 illustrates schematically two overlapping web materials 1 and 2 at least one of which comprising heat fusible material. The webs may be a fibrous nonwoven material, a plastic film or laminates thereof. A web material may further comprise two or more material layers. The overlapped portion between the two webs is denoted with the numeral 3. The webs 1 and 2 are in the overlapped portion joined by a bonding pattern 4 comprising a plurality of bonding elements. The bonding is accomplished by any method known in art in which the heat fusible material is caused to melt and to bond the webs 1 and 2 together, for example ultrasonic welding, heat bonding or the like. The thus bonded overlapped portion 3 forms a seam joining together the two web materials 1 and 2. The seam is in FIG. 1 located in the same plane as the two web materials. Both webs have portions extending outside the overlap.

Figure 4:
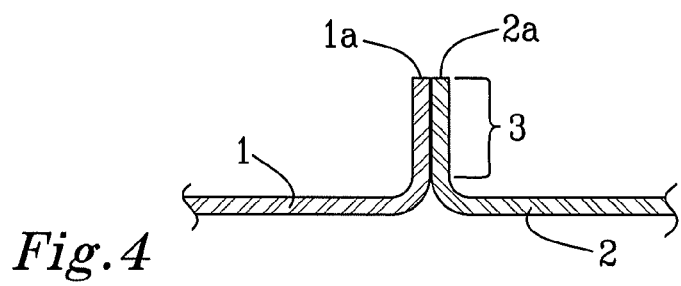
FIG. 4 is a side view of a butt seam between two web materials in which the seam protrudes perpendicularly from the plane of the web materials.

FIGS. 3 and 4 illustrate two main type of seams for joining two web materials, wherein FIG. 3 shows the "plane" seam as in FIG. 1 and FIG. 4 shows a "butt" seam type, in which the seam protrudes from the plane of the web materials 1 and 2. The bonding pattern according to the invention may used for both types of seams, however is especially applicable to "plane" seams as in FIGS. 1 and 3.

In FIG. 1 the bonding pattern 4 extends over the entire width of the overlapped portion 3. Thus the respective side edges 1a and 2a of the two web materials are located close to the edges of the bonding pattern 4 and the width, w, of the bonding pattern 4, defined as the distance between the longitudinal outer limiting margins of the bonding pattern 4, is basically the same as the width of the overlapped portion 3. This is an appealing look for a seam, but may be difficult to achieve in a process line running at high speeds.

It is favourable to have both web materials 1 and 2 covering the entire bonding pattern 4. If the bonding pattern 4 extends outside the overlapped portion 3, no bonding will occur in this region which means that the bonding area gets smaller and the energy level increases in the actual bonding area, which may cause burn through of the material. If on the other hand the bonding pattern terminates a considerable distance inside a side edge of the overlapped portion, this unbonded side edge may protrude out of the plane of the seam, which is undesired both from aesthetical point of view and also for comfort reasons, especially if this protruding edge is located in contact with the skin of the wearer.

An example of a bonding pattern according to the invention is shown in FIG. 1. The bonding pattern 4 comprises a first bonding pattern 5 extending in longitudinal direction, y, along the overlapped portion 3 and a second bonding pattern 6 extending in longitudinal direction along one side edge 1a of the overlapped portion 3 of the web materials. In the embodiment shown in FIG. 1 the first bonding pattern 5 extends along the opposite side edge 2a of the overlapped portion 3, while in an alternative embodiment second bonding patterns may be provided along both side edges 1a and 2a with the first bonding pattern 1 located between the two second bonding patterns 6. Thus the term "bonding pattern 4" as used herein refers to the combined first and second bonding pattern 5 and 6 including areas between the first and second bonding pattern.

The first and second bonding patterns 5 and 6 extend alongside each other substantially in parallel.

The first bonding pattern 5, which is to be seen as the main bonding pattern, has relatively large bonding elements 5a to ensure a strong bonding effect, while the second bonding pattern 6, the edge bonding pattern, has relatively smaller bonding elements 6a. Generally the bonding elements 5a of the first bonding pattern 5 have a mean bonded area that is at least 2 times larger than the mean bonded area of the bonding elements 6a of the second bonding pattern 6. In further embodiments the bonding elements 5a of the first bonding pattern 5 have a mean bonded area that is at least 2.5 times, preferably at least 3 times and more preferably at least 4 times larger than the mean bonded area of the bonding elements 6a of the second bonding pattern 6.

The second bonding pattern 6 comprises relatively densely arranged bonding elements 6a and the bonded area of the second bonding pattern 6 should occupy more than 30% of the combined bonded area of the first bonding pattern 5 and the bonded area of the second bonding pattern 6. This applies both when only one second bonding pattern 6 is present and when two second bonding patterns, one along each side edge, are provided. When two second bonding patterns 6 are provided, the sum of the bonded area of the two second bonding patterns should thus occupy more than 30% of the combined bonded area first bonding pattern 5 and the bonded area of the two second bonding patterns 6.

In certain embodiments the bonded area of the second bonding pattern 6 should occupy at least 50%, preferably at least 60%, of the total bonded area occupied by the combined first and second bonding pattern. In further aspects of the invention the bonded area of the second bonding pattern should occupy not more than 75% of the total bonded area occupied by the combined first and second bonding pattern.

The bonding elements 6a of the second bonding pattern 6 have, in one aspect of the invention, a mean area of not more than 4 $mm^2$, preferably not more than 3 $mm^2$ and more preferably not more than 2 $mm^2$.

The second bonding pattern 6 thus comprises a plurality of relatively small bonding elements 6a relatively densely arranged. Since there is a certain risk that small bonding elements do not always weld the two web materials 1 and 2 together, it is an advantage to have many small bonding elements arranged relatively densely together, to ensure that a sufficient welding effect is obtained by the second bonding pattern. The fact that a certain small percentage of the bonding elements 6a may not weld the web materials 1 and 2 together is then no big problem, as long as there are a certain amount of other bonding elements 6a in the bonding pattern that do.

The second bonding pattern 6 provides for a seam edge with an appealing finish with no protruding edges and with no tear indications, which improves the total strength of the seam.

The first bonding pattern 5 constitutes the main bonding pattern providing overall bonding strength to the seam. The relatively large bonding elements 5a run a considerably smaller risk of not providing a sufficient welding effect of the two web materials 1 and 2, and they may therefore be more sparsely distributed than those of the second bonding pattern 6, without compromising the bonding strength.

The invention is applicable to all bonding patterns accomplished by forwarding the web materials through a bonding apparatus, such as an ultrasonic welding apparatus, a heat bonding apparatus or the like. Such bonding apparatuses usually comprise at least one patterned roll.

It is an important feature of the bonding pattern according to the invention that there is a relatively even contact area across the seam at any given point in the lengthwise direction of the bonding pattern 4. The contact area is the weighted mean value of the area of contact between the bonding apparatus, for example an ultrasonic horn and a patterned anvil roll, and the web materials to be bonded.

Figure 5:
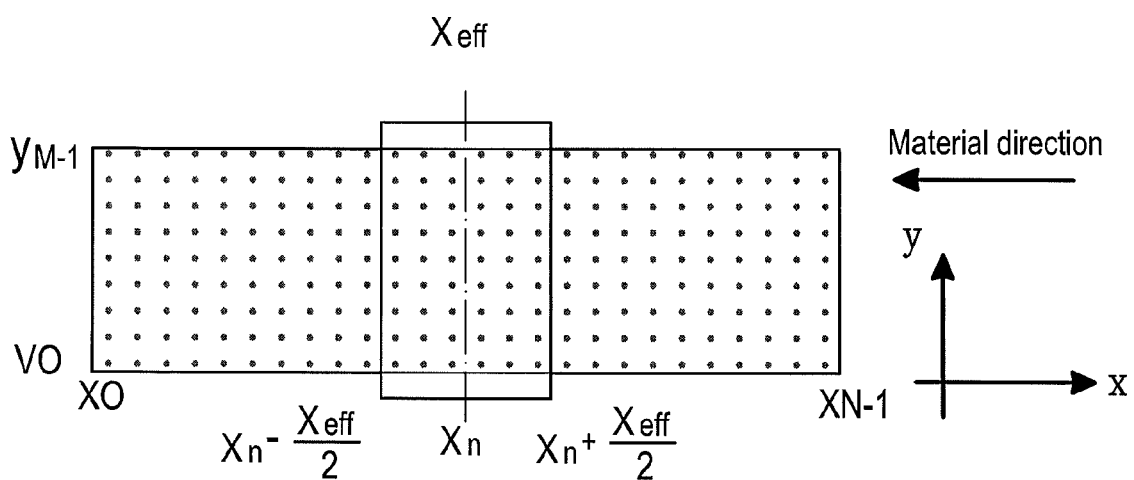
FIG. 5 is an image of bonding pattern (not part of this invention) illustrating the contact area measures.

With reference to FIG. 5, which illustrates an image of a contact pattern (not part of the present invention) illustrating the contact area calculations, a parameter $x_{eff}$ is defined based on a predetermined contact length between the web materials to be bonded and the bonding apparatus, for example in the nip between an ultrasonic horn and a patterned anvil roll. This parameter $x_{eff}$ is in the calculations assumed to be 4 mm, which has shown to be a standard value for commonly available bonding equipments of this kind. A weight function $w_n(x)$ is introduced since not the entire area of contact is in maximum contact with the web materials, and thus the entire area of contact is found as a weight function. The choice of weight function is defined over a certain interval and is defined below in equation (1).

$$w_n(x)\left(1 - A\left(1 - \cos\left|\frac{x - x_n}{B}\right|\right)\right)^2 - x_{eff}; -\frac{x_{eff}}{2} \leq x - x_n \leq \frac{x_{eff}}{2}. \quad (1)$$

As said above $x_{eff}$ is for the purpose of this invention assumed to be 4 (mm). For the constants A and B the following values are used in the calculations: A=5000 and B=0, 1. Even for bonding equipments having $x_{eff}$ smaller or larger than 4 mm the values of $x_{eff}$, A and B may anyhow be used for the purpose of this invention.

The boundary conditions of $w_n(x)$ are set such that the compression has a maximum at the center of the contact area and such that the compression of the outer edges of the contact area is far less.

The weight function $w_n(x)$ is used for calculating the weighted mean value of the area of contact between the bonding apparatus (for example ultrasonic horn and pattern roll) and the web materials as seen in a transverse direction of the seam This weighted mean value is defined as the contact area according to the invention, and can for example be calculated by means of an image analysis of a bonding pattern as described below.

A scanning of the bonding pattern is made using a resolution of 1200 dpi (dots per inch). The pattern is evaluated as a normalized inverted black and white image with the pattern coloured black. Therefore a function defining the pattern image has to be introduced (eq. 2).

$$\gamma_{nm} = \quad (2)$$

$$\gamma(x_n, y_m) = \begin{cases} 1, & \text{if the pixel in } (x_n, y_n) \text{ is located in pattern} \\ 0, & \text{if the pixel in } (x_n, y_n) \text{ is not located in pattern} \end{cases}$$

The normalized and weighted contact area is now defined as $$\hat{X}_n = \frac{\sum_{i=n-\varepsilon}^{n+\varepsilon} X_i w_n(x_i)}{\sum_{j=n-\varepsilon}^{n+\varepsilon} w_n(x_i)}, \text{ (multiply by 100 to get the percentage)} \quad (3)$$

where $$X_i = \frac{1}{M} \sum_{m=0}^{M-1} \gamma_{im}, \quad (4)$$

and $\varepsilon$ is the integer number of pixels within the length $$\frac{x_{eff}}{2}$$

of the pattern image.

The contact area of the bonding pattern should be between 10 and 30% of the width, w, of the bonding pattern 4 at any given point along the length of the bonding pattern. In preferred embodiments the contact area is between 10 and 25% and preferably between 13 and 20% of the width, w, of the bonding pattern 4 at any given point along the length of the bonding pattern.

The contact area in % of the bonding pattern 4 shown in FIG. 1 is illustrated in FIG. 2, and as is seen the contact area for this specific bonding pattern varies within a very narrow interval, between 15.4 and 16%.

An even contact area along the length of the bonding pattern 4 means that the bonding strength along the seam is even and the points at which tear formations can begin are minimized.

The bonding pattern illustrated in FIG. 1 has along a side edge 1a a second bonding pattern 6 comprising a plurality of small bonding elements 6a each having a mean area of not more than 2 mm². These bonding elements 6a are arranged in two or more (four in FIG. 1) longitudinal rows in which the bonding elements 6a are located in a staggered relationship with respect to the bonding elements of the adjacent row. The number of bonding elements 6a in the second bonding pattern is between preferably 8 and 50 per cm².

The first bonding pattern 5 comprises a plurality of bonding elements 5a, which are larger than and more sparsely distributed than the bonding elements 6a of the second bonding pattern. The number of bonding elements in the first bonding pattern 5 is between 4 and 25 per cm². The bonding elements 5a are arranged in two (or more) longitudinal rows in which the bonding elements are located in a staggered relationship to each other and offset with respect to the bonding elements 6a of the second bonding pattern 6 as seen in the transverse direction of the seam. This configuration of bonding elements 5a and 6a provides for the even contact area along the seam as discussed above.

The bonding density of the first bonding pattern is at least 2% and not more than 60%, preferably not more than 40%. The bonding density of the second bonding pattern is between 5 and 60%, preferably between 10 and 50%. Preferably the bonding density of the second bonding pattern 6 is higher than of the first bonding pattern 5.

The bonding elements of the second and/or the first bonding patterns may be circular or have any other optional geometrical shape. Circular bonding elements tend to give less tear indications than elongated bonding elements, which improves the bonding strength of the seam.

The width, w, of the bonding pattern 4 in transverse direction can be made substantially equal to or only slightly smaller than the width of the overlapped portion 3 in transverse direction. This means that the side edges 1a and 2a of the web materials 1 and 2 are prevented from protruding out of the plane of the web materials, but are effectively bonded down by the bonding patterns 5, 6.

The width of the bonding pattern 4 as well as of the overlapped portion 3 in the transverse direction is preferably between 5 and 40 mm, more preferably between 6 and 20 mm.

Figure 6:
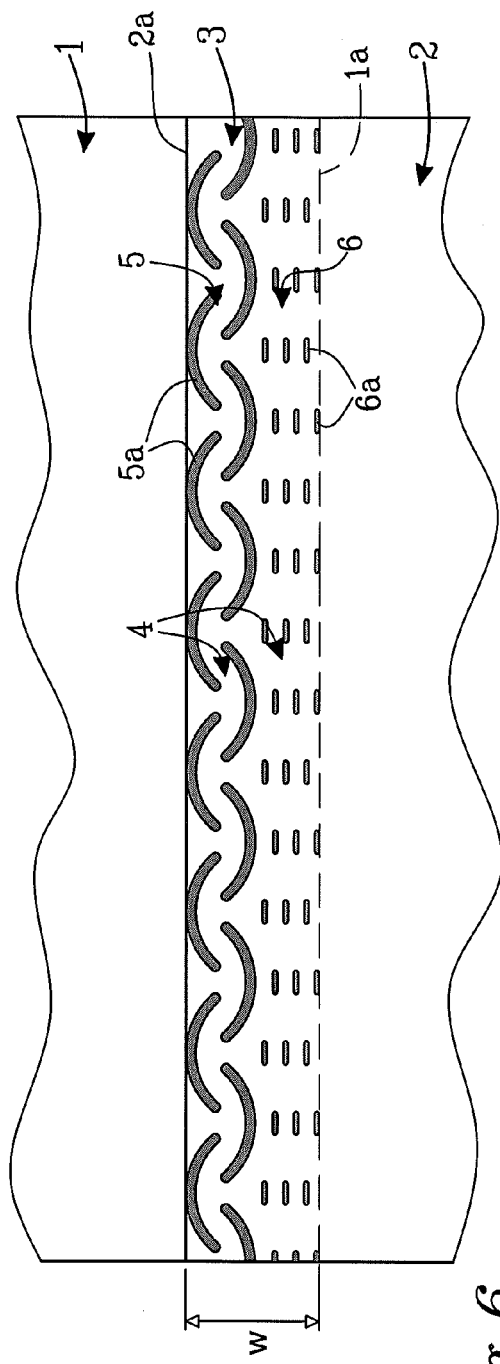
FIG. 6 shows a seam having a bonding pattern according to another embodiment of the present invention.

FIG. 6 shows a further embodiment of a bonding pattern 4 according to the invention. The bonding pattern illustrated in FIG. 7 comprises a first bonding pattern 5 in the form of a plurality of "banana"-shaped bonding elements 5a oriented in lengthwise direction of the seam and arranged in two staggered rows with their concave sides facing each other. The bonding pattern 4 further comprises a second bonding pattern 6 comprising a plurality of small bonding elements 6a in the form of short lines oriented in lengthwise direction of the seam. The bonding elements 6a are arranged in transverse rows located opposite to the spacing between adjacent bonding elements 5a in each of the staggered rows of bonding elements 5a.

Figure 7:
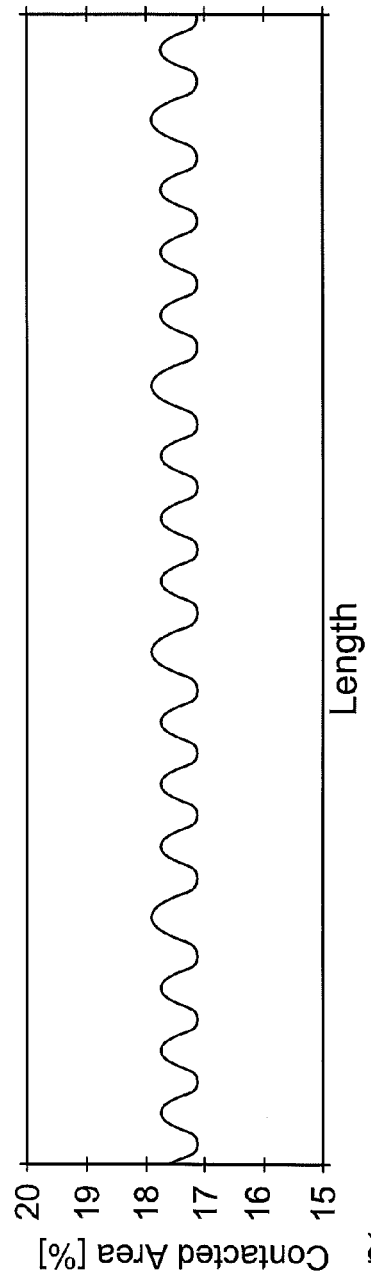
FIG. 7 is a graph showing the lengthwise surface coverage of the bonding pattern of FIG. 6.

This configuration of bonding elements 5a and 6a shown in FIG. 6 also provides for the even contact area along the seam as discussed above. The contact area for the bonding pattern of FIG. 6 is illustrated in FIG. 7 and is between 17 and 18%.

The invention is especially applicable to web materials having a combined basis weight between 25 and 130 g/m$^2$ in the overlapped portion. At least one web material is in one embodiment of the invention an elastic material, such as an elastic film, an elastic nonwoven or an elastic laminate therefrom. An elastic material is defined as a material having an elasticity of at least 30% in the elasticity test described below.

Figure 9:
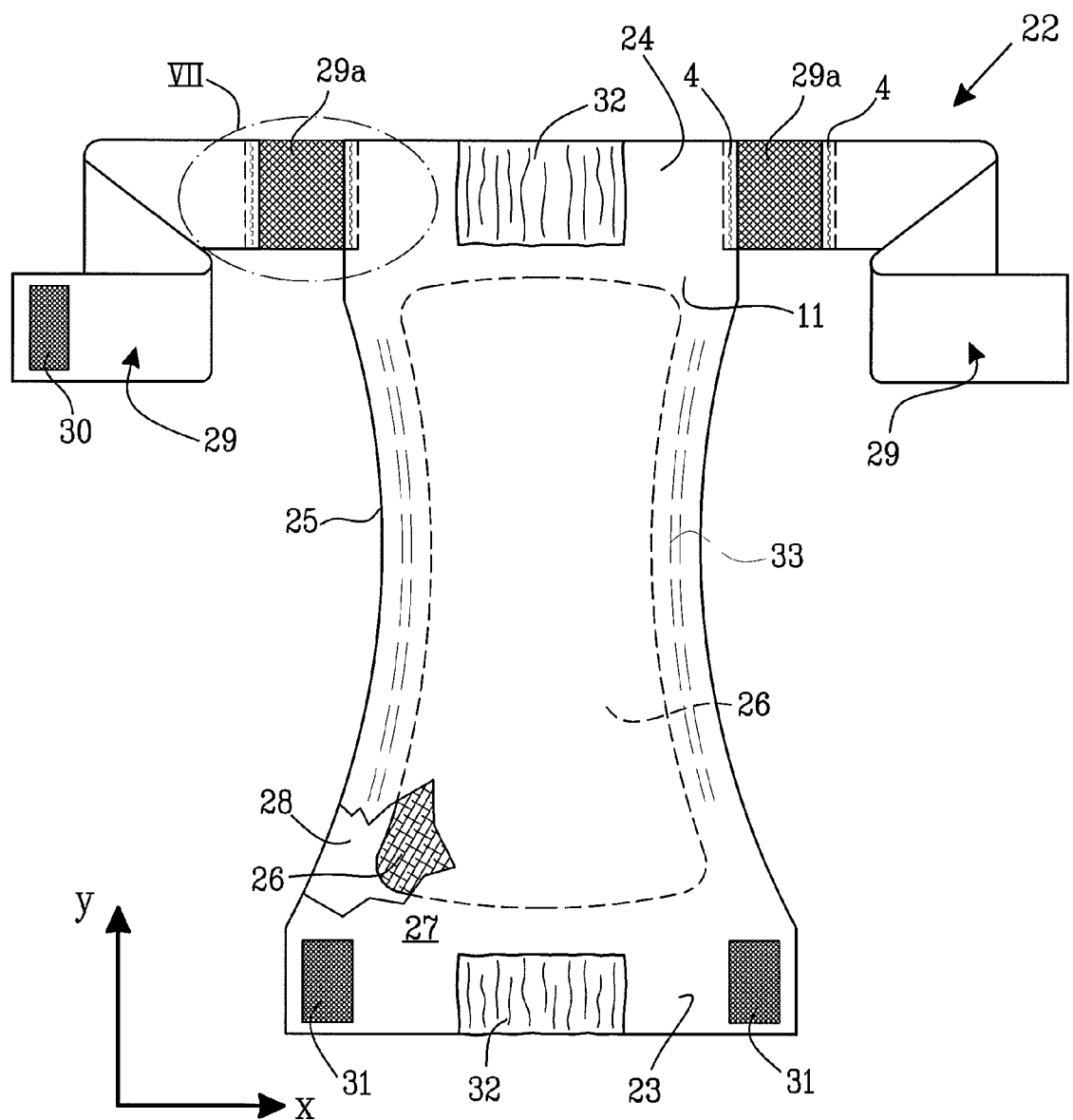
FIG. 9 is a plan view of a belted diaper.
Figure 10:
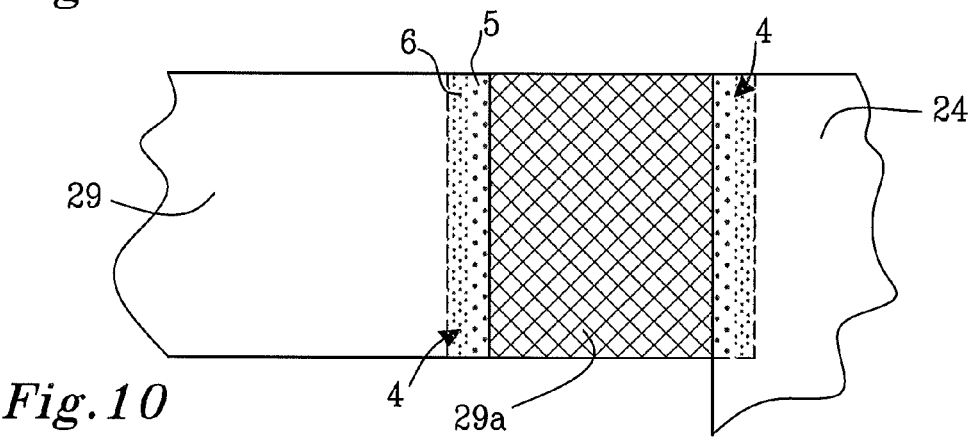
FIG. 10 shows on a larger scale a detail from FIG. 9, namely the attachment of the belt to the article.

One important application of the invention is in personal care absorbent articles such as diapers, incontinence guards, sanitary napkins and the like comprising an absorbent structure and web materials joined together to form different components of the articles. Examples of seams in absorbent articles which may use the bonding pattern according to the invention are shown in FIGS. 8-10.

Figure 8:
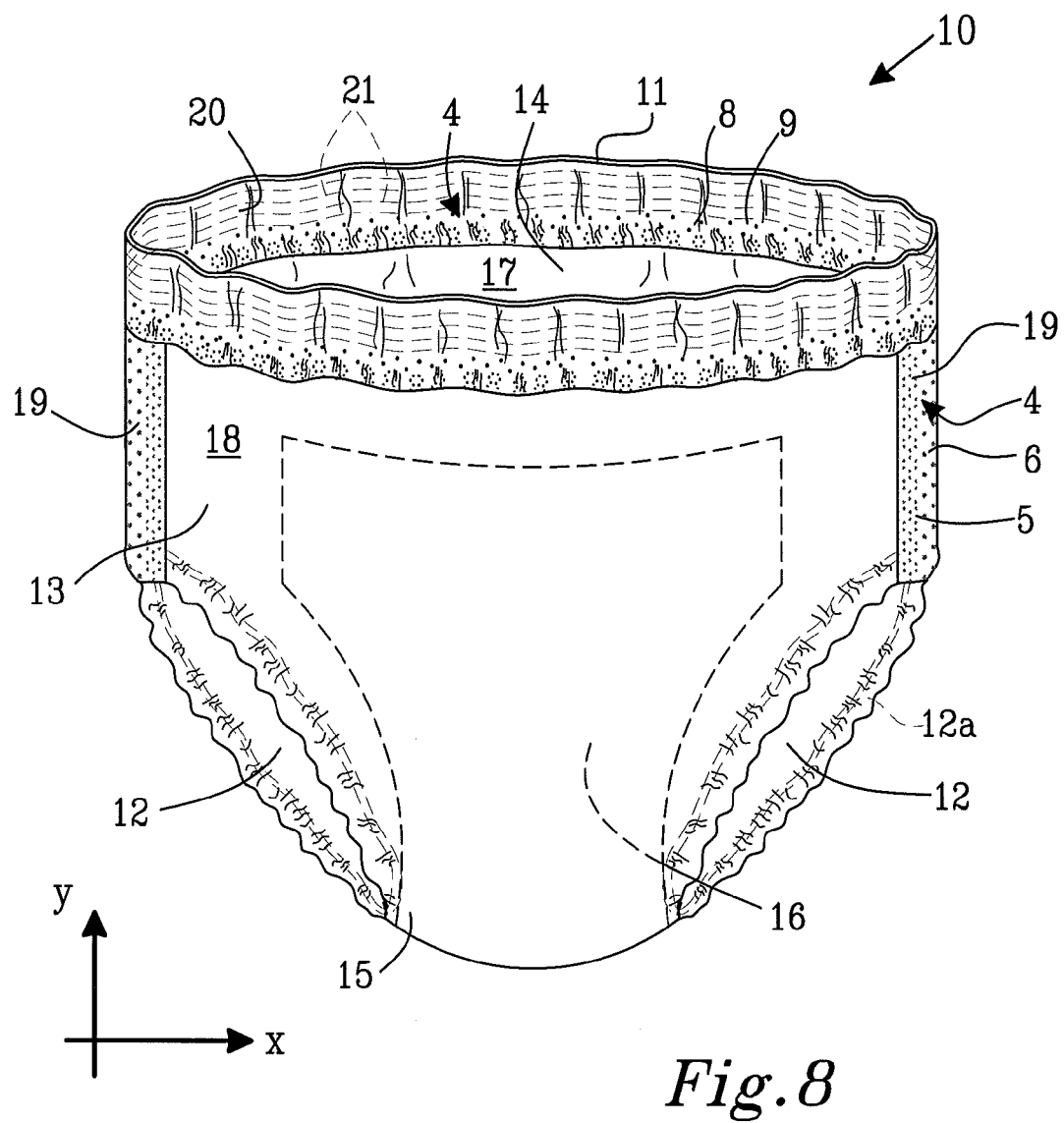
FIG. 8 is a perspective view of a pant-type absorbent article.

FIG. 8 shows a pant-type absorbent article 10 having a defined waist opening 11 and a pair of leg openings 12 and which is pulled onto the body of the wearer by inserting the legs into the leg openings and pulling the article up over the waist. Examples of such pant-type absorbent article are pant diapers, training pants, swim pants, sanitary pants and incontinence pants worn by incontinent adults. The article will in the following be referred to as a "pant diaper". The article has a longitudinal direction y and a transverse direction x.

The pant diaper comprises a front body panel 13, which is the part of the pant diaper that in use is intended to extend over the stomach and front hip area of the wearer. The article also comprises a back body panel 14, which is the part of the article that in use is intended to extend over the back and the rear hip area of the wearer. The crotch portion 15 of a pant diaper article is the part of the diaper that in use is intended to extend through the wearer's crotch area, between the legs.

An absorbent core 16 is disposed in the crotch portion 15 and extends into the front and back body panels 13 and 14. The absorbent core is disposed between an inner coversheet 17 and an outer coversheet 18.

The term "inner coversheet" refers to the liquid permeable material sheet forming the inner cover of the absorbent article and which in use is placed in direct contact with the skin of the wearer. The inner coversheet can comprise a nonwoven material, e.g. spunbond, meltblown, carded, hydroentangled, wet-laid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner coversheet material may further be composed of tow fibres, which may be bonded to each other in a bonding pattern, as e.g. disclosed in EP-A-1 035 818. Further examples of inner coversheet materials are porous foams, apertured plastic films etc. The materials suited as inner coversheet materials should be soft and non-irritating to the skin and be readily penetrated by body fluid, e.g. urine or menstrual fluid. The inner coversheet may further be different in different parts of the absorbent article.

The "outer coversheet" refers to the material forming the outer cover of the absorbent article. The outer coversheet may be the same or different in different parts of the absorbent article. At least in the area of the absorbent core the outer coversheet comprises a liquid impervious material a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The outer coversheet material may be breathable so as to allow vapour to escape from the absorbent core, while still preventing liquids from passing therethrough. Examples of breathable outer coversheet materials are porous polymeric films, nonwoven laminates of spunbond and meltblown layers and laminates of porous polymeric films and nonwoven materials. Preferably, the outer coversheet comprises a nonwoven material on at least the garment-facing surface thereof.

The "absorbent core" is the absorbent structure disposed between the two coversheets of the absorbent article in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent compoelements including particles, fibres, flakes, spheres, and the like.

A high liquid storage capacity is provided by the use of high amounts of superabsorbent material. For an absorbent core comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

The front and back body panels 13 and 14 or those parts thereof that are located outside the absorbent core region may have different material composition than the crotch portion 15. Thus according to one embodiment the areas of the front and back body panels 13 and 14 which are located outside the absorbent core region may be composed of for example a laminate material having a body facing side and a garment facing side, while a liquid impervious outer coversheet and/or a liquid pervious inner coversheet only is present in the absorbent core region. In other embodiments the inner and outer coversheets are the same in the front and back body panels 13 and 14 as well as in the crotch region 15.

The entire or part of the front and back body panels may be of elastic material. The elastic web material may be in the form of elastic nonwoven materials, nonwoven materials which per se are inelastic, but which have been elastified by means of elastic threads etc., elastic laminates composed of external layers of fibrous material and a middle elastic film layer.

The front and back panels 13 and 14 are joined along longitudinal side edges so as to form side seams 19. The front and back panels 13 and 14 can either be joined with the inner coversheets 17 of either the front or back panel facing the outer coversheet 18 of the opposite panel. In such case the side seam will be in the same plane as the adjacent portions of the front and back panels facing inwards in the side seams, as is shown in FIG. 8. Alternatively they are joined with the inner coversheets of the front and back panels facing inwards, wherein the side seam 19 will protrude from the plane of the front and back panels.

The front and back panels 13 and 14 are joined along the side seams 19 by a bonding pattern 4 according to the invention, comprising a first bonding pattern 5 and a second edge bonding pattern 6.

An elastic waistband 20 is secured to the front and back panels 13 and 14 along the waist opening. In its most common form the elastic waistband 20 comprises a substantially nonelastic nonwoven material that is elasticized by elongate elastic members 21, such as elastic threads or bands, contractably affixed between material layers, such as nonwoven materials. Alternatively the elastic waistband comprises an elastic nonwoven or an elastic film-nonwoven laminate. The elastic waistband 20 is joined to the front and back panels 13 and 14 by a bonding pattern 4 according to the invention. The bonding pattern according to the invention is especially adapted for joining a waistband to the front and back panels and accomplishes a strong seam at the same time as the finish along the seam edge is appealing with no protruding edges.

The leg openings 12 are also elasticized, said elastification is usually accomplished by a plurality of elastic members 12a, such as elastic threads, which are contractably affixed between the outer and inner coversheets.

FIGS. 9 and 10 of the drawings show an embodiment of an absorbent garment in the form of a diaper or incontinence guard 22 comprising a first body panel 23 and a second body panel 24, and a crotch portion 25 there between. An absorbent core 26 is disposed in the crotch portion 25 and extends into the first and second body panels 23 and 24. The absorbent core 26 is disposed between an inner coversheet 27 and an outer coversheet 28. The inner and outer coversheets and the absorbent core may be of the materials mentioned above with respect to the pant diaper. The garment has a longitudinal direction y and a transverse direction x.

A pair of belt members 29 are attached to the waist portion of second body panel 24 and are intended to be wrapped around the waist of the wearer of the garment and fastened together by means of first fastening means 30, for example a mechanical fastener, especially a hook fastener of a hook-and-loop fastening means. The external surface of the opposite belt member, especially if this comprises a fibrous nonwoven, may function as a loop member.

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook-and-loop fasteners are for example available from Velcro, USA.

Alternatively the first fastening means 30 is an adhesive fastening means such as a tape tab, wherein the external surface of opposite belt member 29 may be of a material to which the tape can adhere, as for example described in WO 01/00129.

The width of the belt members 29 should be from 5 to 20 cm, preferably from 7 to 15 cm. The belt members 29 are preferably made from a laminate of a carrier material, which forms the external surface of the belt, and a soft nonwoven, which forms the inside of the belt which is intended to be in direct contact with the skin of the user.

A suitable nonwoven material can be a spunbond material of e.g. polypropylene or polyethylene fibres. Conjugate fibres may also be used. Another suitable nonwoven material is formed from a carded thermobonded material of e.g. polypropylene, polyester or conjugate fibres.

The carrier material should be adapted to function as a reception surface for the fastening means 30. In case the fastening means is a hook fastener a nonwoven material may be used as a carrier material. In case the fastening means 30 is a tape tab, a plastic film is suitable as carrier material.

The first body panel 23, which normally is the front body panel, is then passed between the legs of the wearer and fastened to the outside of the belt members 29 by means of second fastening means 31 provided at the lateral edges of the waist portion of the front panel 23. These second fastening means 31 are mechanical fasteners, such as hook fasteners, or adhesive tape fasteners.

Each belt member 29 comprises at its proximal end adjacent the first body panel 24, an elastic region 29a. Said elastic region 29a may be in the form of an elastic web material such as an elastic film, an elastic nonwoven, an elastic laminate or the like. The elastic laminate may be a laminate between two or more nonwoven layers, two or more film layers or a combination of film and nonwoven layers.

Examples of elastic laminates suitable for forming said elastic regions 29a are any elastic laminate known in the art. One group of elastic laminates are so called "stretch-bonded" laminates, in which the elastic layer is stretched in at least one direction before laminating it with one or more inelastic layers. After the tension is removed from the elastic layer it can freely retract to its untensioned state, and the inelastic layer(s) laminated thereto become gathered, giving a three-dimensional puckering.

Another group of elastic laminates are so called "neck bonded" laminates, which refer laminates in which an elastic material is bonded to a non-elastic material while the non-elastic member is extended under conditions reducing its width or necked. "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO/047488, in which inelastic nonwoven layers are laminated to an elastic film layer, and the laminate is stretched above the point of failure of the nonwoven materials, so that the inelastic layers break.

Examples of elastic laminates are described in EP-B-0 646 062, WO 98/29251, WO 03/000165 and U.S. Pat. No. 5,226, 992. Examples of commercially available elastic laminates are Fabriflex 306 from Tredegar and PK 6358 from Nordenia.

The elastic regions 29a preferably have an elasticity of at least 30% as measured in the elasticity test as described below.

Alternatively the elastic regions 29a comprises one or more elastic threads or strips contractably affixed between web material layers.

In an alternative embodiment only one belt member 29 is provided with an elastic region 29a.

A waist elastic member 32 extends in transverse direction, x, along at least part of the waist portion of each body panel 23 and 24. The waist elastic member may be an elastic web material such as an elastic laminate, an elastic film or the like contractably attached between the inner and outer coversheets, to the external side of the outer coversheet or to the wearer facing side of the inner coversheet. Alternatively it comprises two or more elastic threads or strips contractably affixed between the outer and inner coversheets.

The leg openings are also elasticized, said elastification is usually accomplished by a plurality of elastic members 33, such as elastic threads, which are contractably affixed between the outer and inner coversheets.

The elastic region 29a is bonded to the respective belt member 10 and/or to the first body panel 24 side edge by a bonding pattern 4 according to the invention.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the web material should have a permanent relaxation after elongation of less than 10% after being exerted to an elongation of 30% in the tensile tester above. An elongation of 30% means an elongation to a length that is 30% longer than the initial length of the sample.

Although only two examples of a bonding patterns and a few examples of applications for the bonding pattern according to the invention have been described in detail above, those skilled in the art will readily understand that many modifications are possible both with respect to the configuration of the bonding pattern and applications therefore.

The invention claimed is:

1. A seam in a personal care absorbent article comprising an absorbent structure and first and second web materials comprising heat fusible material joined together by a bonding pattern, the first web material having a side edge overlapping with a side edge of the second web material, wherein an overlapped portion is formed where said web materials overlap, said web materials in said overlapped portion being bonded by a bonding apparatus in which the web materials are forwarded through the bonding apparatus, said bonding pattern extending over at least a part of the overlapped portion to form said seam, said bonding pattern comprising a plurality of bonding elements spaced from each other in a repeating pattern, said overlapped portion having a pair of longitudinal side edges defined by said overlapping side edges of the web materials, said bonding pattern having a width defined by outer limiting margins of the bonding pattern, wherein said bonding pattern comprises a first bonding pattern extending in a longitudinal direction along at least a part of the overlapped portion, and at least one second bonding pattern extending in a longitudinal direction along and adjacent at least a part of at least one of said side edges of said overlapped portion, wherein the bonded area of said second bonding pattern occupies at least 50% of the combined bonded area of the first bonding pattern and the bonded area of the second bonding pattern, the bonding elements of the first bonding pattern have a mean area that is at least 2 times larger than the mean area of the bonding elements of the second bonding pattern, and a contact area of the bonding pattern, as seen in a transverse direction of the seam, is between 10 and 30% of the width of the bonding pattern at any given point along a length of the bonding pattern, wherein the contact area is a weighted mean value of the area of contact between the bonding apparatus and the web materials, and said personal care absorbent article is a pant garment comprising a first body panel, a second body panel and a crotch portion there between, said first and second body panels being joined together to form side seams and further being provided with an elastic waistband, said waistband being joined to the first or second body panel in an overlapped manner to form said seam.

2. The seam as claimed in claim 1, wherein a bonded area of the second bonding pattern occupies at least 60% of a total bonded area occupied by the combined first and second bonding patterns.

3. The seam as claimed in claim 1, wherein a bonded area of the second bonding pattern is not more than 75% of a total bonded area occupied by the combined first and second bonding patterns.

4. The seam as claimed in claim 1, wherein the bonding elements of the first bonding pattern each has a mean bonding element area that is at least 2.5 times larger than a mean bonding element area of the bonding elements of the second bonding pattern.

5. The seam as claimed in claim 1, wherein the bonding elements of the second bonding pattern each has a bonding element area of not more than 4 mm$^2$.

6. The seam as claimed in claim 1, wherein the contact area of the bonding pattern, as seen in the transverse direction of the seam, is between 10 and 25% of the width of the bonding pattern at any given point along the length of the bonding pattern.

7. The seam as claimed in claim 1, wherein the second bonding pattern comprises a plurality of small bonding elements each having a mean area of not more than 2 mm$^2$, said bonding elements being arranged in at least two longitudinal rows in which the bonding elements are located in a staggered relationship with respect to the bonding elements of the adjacent row, and wherein the number of bonding elements in the second bonding pattern is between 8 and 50 per cm$^2$.

8. The seam as claimed in claim 7, wherein the first bonding pattern comprises a plurality of bonding elements arranged in at least two longitudinal rows in which the bonding elements are located in a staggered relationship to each other and offset with respect to the bonding elements of the second bonding pattern as seen in the transverse direction.

9. The seam as claimed in claim 8, wherein the number of bonding elements in the first bonding pattern is between 4 and 25 per cm$^2$.

10. The seam as claimed in claim 1, wherein the bonding elements of the second bonding pattern are circular.

11. The seam as claimed in claim 1, wherein the bonding elements of the first bonding pattern are circular.

12. The seam as claimed in claim 1, wherein said bonding pattern comprises two second bonding patterns, one on each side of the first bonding pattern.

13. The seam as claimed in claim 1, wherein the width of the overlapped portion in a transverse direction is between 5 and 40 mm.

14. The seam as claimed in claim 13, wherein the width of the bonding pattern is between 5 and 40 mm.

15. The seam as claimed in claim 1, wherein said first bonding pattern has a bonding density of at least 2% and not more than 60%.

16. The seam as claimed in claim 15, wherein said second bonding pattern has a higher bonding density than the first bonding pattern.

17. The seam as claimed in claim 1, wherein said second bonding pattern has a bonding density of between 5 and 60%.

18. The seam as claimed in claim 1, wherein said web materials have combined basis weight between 25 and 130 g/m$^2$ in said overlapped portion.

19. The seam as claimed in claim 1, wherein at least one of the web materials is an elastic material.

20. The seam as claimed in claim 1, wherein the seam is located in the same plane as the web materials that are joined together.

21. The seam as claimed in claim 1, wherein said personal care absorbent article is a pant-like garment comprising a first body panel, a second body panel and a crotch portion there between, said first and second body panels being joined together in an overlapped manner to form side seams joined by a bonding pattern as claimed in claim 1.

22. A pant garment comprising an absorbent structure and first and second web materials comprising heat fusible material joined together by a bonding pattern, the first web material having a side edge overlapping with a side edge of the second web material, wherein an overlapped portion is formed where said web materials overlap, said web materials in said overlapped portion being bonded by a bonding apparatus in which the web materials are forwarded through the bonding apparatus, in said bonding pattern extending over at least a part of the overlapped portion to form said seam, said bonding pattern comprising a plurality of bonding elements spaced from each other in a repeating pattern, said overlapped portion having a pair of longitudinal side edges defined by said overlapping side edges of the web materials, said bonding pattern having a width defined by outer limiting margins of the bonding pattern, wherein said bonding pattern comprises a first bonding pattern extending in a longitudinal direction along at least a part of the overlapped portion, and at least one second bonding pattern extending in a longitudinal direction along and adjacent at least a part of at least one of said side edges of said overlapped portion, wherein the bonded area of said second bonding pattern occupies at least 50% of the combined bonded area of the first bonding pattern and the bonded area of the second bonding pattern, the bonding elements of the first bonding pattern have a mean area that is at least 2 times larger than the mean area of the bonding elements of the second bonding pattern, and a contact area of the bonding pattern, as seen in a transverse direction of the seam, is between 10 and 30% of the width of the bonding pattern at any given point along a length of the bonding pattern, wherein the contact area is a weighted mean value of the area of contact between the bonding apparatus and the web material, wherein the pant garment further comprises a first body panel, a second body panel, a crotch portion between the first and second body panels, and an elastic waistband, said first and second body panels being joined together to form side seams and said waistband being joined to the first or second body panel in an overlapped manner to form said seam.

* * * * *